US008463360B2

(12) United States Patent  (10) Patent No.: US 8,463,360 B2
Yamamoto et al.  (45) Date of Patent: Jun. 11, 2013

(54) SURGERY SUPPORT DEVICE, SURGERY SUPPORT METHOD, AND COMPUTER READABLE RECORDING MEDIUM STORING SURGERY SUPPORT PROGRAM

(75) Inventors: Seiji Yamamoto, Hamamatsu (JP); Susumu Terakawa, Hamamatsu (JP); Toshihisa Takai, Hamamatsu (JP); Katsuhiro Sato, Hamamatsu (JP)

(73) Assignee: National University Corporation Hamamatsu University School of Medicine, Hamamatsu-shi (JP)

( * ) Notice: Subject to any disclaimer, the term of this patent is extended or adjusted under 35 U.S.C. 154(b) by 715 days.

(21) Appl. No.: 12/278,954

(22) PCT Filed: Jan. 31, 2007
 (Under 37 CFR 1.47)

(86) PCT No.: PCT/JP2007/051603
 § 371 (c)(1),
 (2), (4) Date: Apr. 26, 2010

(87) PCT Pub. No.: WO2007/091464
 PCT Pub. Date: Aug. 16, 2008

(65) Prior Publication Data
 US 2011/0054300 A1 Mar. 3, 2011

(30) Foreign Application Priority Data
 Feb. 9, 2006 (JP) ................. 2006-032605

(51) Int. Cl.
 *A61B 5/05* (2006.01)
(52) U.S. Cl.
 USPC ............ 600/427; 600/407; 600/410; 600/411
(58) Field of Classification Search
 USPC ......... 600/427, 407, 410–411, 420, 433–434, 600/466–467; 324/306–309
 See application file for complete search history.

(56) References Cited

U.S. PATENT DOCUMENTS

| 5,494,034 A | 2/1996 | Schlöndorff et al. |
| 5,531,520 A | 7/1996 | Grimson et al. |
| 5,617,857 A | 4/1997 | Chader et al. |
| 2002/0002330 A1* | 1/2002 | Vilsmeier ................ 600/407 |
| 2003/0000535 A1 | 1/2003 | Galloway et al. |
| 2003/0163040 A1 | 8/2003 | Gildenberg |
| 2004/0097805 A1* | 5/2004 | Verard et al. ................ 600/428 |
| 2004/0138556 A1 | 7/2004 | Cosman |
| 2005/0096589 A1* | 5/2005 | Shachar .................. 604/95.01 |

FOREIGN PATENT DOCUMENTS

| DE | 10242953 A1 | 3/2004 |
| JP | 55-52749 | 4/1980 |

(Continued)

OTHER PUBLICATIONS

Estermann B et al.: "Non-Invasive 3-D Patient Registration for Image-Guided Skull Base Surgery," *Computers and Graphics*, vol. 20, No. 6, pp. 793-799 (1996).

(Continued)

*Primary Examiner* — Tse Chen
*Assistant Examiner* — Joel F Brutus
(74) *Attorney, Agent, or Firm* — Marshall, Gerstein & Borun LLP

(57) ABSTRACT

Presentation of images showing with high resolution the state of a surgical field during surgery is realized with a simple configuration. When performing surgery, a three-dimensional model is generate based on MRI images of a patient captured prior to surgery, and three-dimensional coordinates of each location on a surface of the patient are measured by scanning a laser beam over the surface and detecting laser beam reflected therefrom, and correspondence is made with the MRI image for each location of the surface (frameless/markerless: steps 100 to 116), the position of a surgical instrument is also detected by the laser beam, the position of the surgical instrument derived, and images of the surgical instrument combined onto the MRI images and displayed during surgery (steps 120 to 130).

9 Claims, 6 Drawing Sheets

FOREIGN PATENT DOCUMENTS

| JP | 2-503519 | 10/1990 |
|---|---|---|
| JP | 9-511430 | 11/1997 |
| JP | 2005-518854 | 6/2005 |
| WO | WO-94/24933 A1 | 11/1994 |
| WO | WO96/07144 | 3/1996 |
| WO | WO03/073915 | 9/2003 |

OTHER PUBLICATIONS

Supplementary Partial European Search Report ssued in European Application No. EP 07 70 7789, mailed Mar. 17, 2010.

Annex to the European Search Report on European Patent Application No. EP 07 70 7789, mailed Mar. 17, 2010.

Medtronic SNT, "StealthStation," as found at http//www.stealthstation.com/physician/neuro/library/teron.jsp, Sep. 2, 2005.

Medtronic SNT, "SonoNav", as found at http//www.stealthstation.com/phyusician/neuro/library/sononav.jsp, Sep. 2, 2005.

International Search Report in corresponding PCT/JP2007/051603 dated Apr. 24, 2007.

Written Opinion in corresponding PCT/JP2007/051603 dated Apr. 24, 2007.

International Preliminary Report for Patentability in corresponding PCT/JP2007/051603 dated May 27, 2008.

* cited by examiner

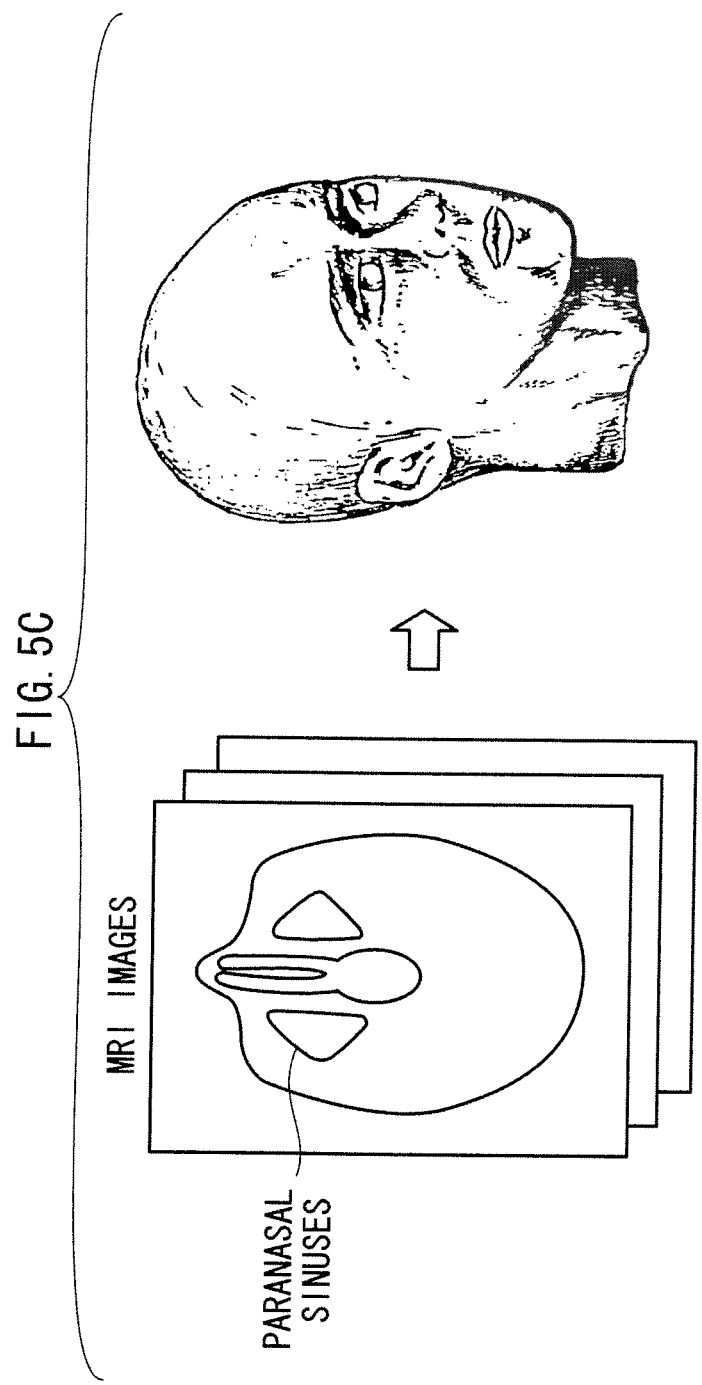

SURGERY SUPPORT DEVICE, SURGERY SUPPORT METHOD, AND COMPUTER READABLE RECORDING MEDIUM STORING SURGERY SUPPORT PROGRAM

TECHNICAL FIELD

The present invention relates to a surgery support device, method and program, and in particular to a surgery support device for supporting execution surgery by displaying on a display plural high resolution tomographic images of the surgical field captured prior to surgery, to a surgery support method, and to a surgery support program for providing a computer with the functionality of the surgery support device.

RELATED ART

In MRI: Magnetic Resonance Imaging (a) so called NMR-CT: Nuclear Magnetic Resonance-Computed Tomography) a nuclear magnetic resonance phenomenon of the spin of atomic nuclei within a living subject in a static magnetic field is used to obtain tomographic images of the living subject. There are advantages with such a method that there are no exposure by irradiation with radiation as in X-ray CT imaging, such as there is no influence from the bones, and tomographic images can be obtained with high resolution in a chosen direction. Hence, MRI is used in various medical fields, such as in surgery and in investigations (the tomographic images obtained from imaging with Nuclear Magnetic Resonance-Computed Tomography are referred to as MRI images here below).

In surgery, for example, MRI images are sometimes captured of the patient prior to surgery and the actual surgery itself proceeds while repeatedly comparing the surgical field itself and the MRI images, in order to improve the accuracy of the surgery. In human organs, such as the brain, there are functionally important areas (eloquent areas) (for example the motor area, sensorimotor area, language area, visual cortex, auditory area etc.), and the position and manner in which each eloquent area is partitioned is investigated in advance, and maps with the partitioning state of each eloquent area are displayed on MRI images of the head, for reference during surgery (this is called functional mapping MRI).

However, when surgery is actually carried out, the facial bone and skull bone of the head are covered, and is difficult to use an expanded surgical field to perform surgery with the whole area in view, since organs such as the brain are important organs including complex structure. Therefore, in stereotactic neurosurgery, and paranasal pituitary surgical excision, and in ENT (Ear Nose and Throat) surgery, such as endoscopic surgery to the paranasal sinus, three-dimensional awareness of where manipulation is currently being made, is required in order to perform safe and accurate surgery within a small, confined surgical field. Similar problems are also encountered in endoscopic surgery to the chest, lumber region, and urinary tract.

In stereotactic neurosurgery, for example, a frame designed to facilitate subsequent surgical operation is mounted to the patient (subject) prior to surgery (such a frame is not just for fixing the head of the patient but is a frame with a scale attached, called a "frame for stereotactic neurosurgery" or "fixing device for stereotactic neurosurgery"), and MRI and CT scans are taken of the area around the surgical field including the frame, and three-dimensional coordinates of each position in the brain are computed from the captured images, and the movement distance for reaching the target position of the operation is calculated, from an origin determined in advance. Then in the operation the route to reach the target position is secured, and, for example, an instrument is inserted through one of the various holes in the head, or a hole is opened in a chosen place in the skull bone (for example with a 1.2 mm to 1.6 mm diameter). At the target position a portion of a tumor is sampled for investigation (a biopsy), electrocoagulation is carried out, a stimulation electrode is place, or a hemorrhage is aspirated.

However, it is not possible during surgery to verify and confirm in real time that the target has actually been reached. Therefore confirmation is made using images from imaging the distal end of the inserted needle in a CT room, or in an MRI room (called CT/MR guided stereotactic neurosurgery). There are a great number of limitations to the location and instruments in such CT/MR guided stereotactic neurosurgery. In addition it is necessary to penetrate the skin with sharp fasteners for mounting the frame, and even though a local anesthetic is used, this procedure has accompanying discomfort and imposes a considerable strain on the patient. Furthermore, while a CT/MRI apparatus can be provided in the operating room (called intraoperative CT/MRI) the problem is that this requires significant capital investment, such as in refurbishment of the operating room and the like.

Endoscopes are also used for confirmation in ENT surgery, and such surgery is not generally CT/MR guided surgery. There is limited visibility in such endoscopic surgery, the overall picture is difficult to see, and is difficult to determine the accurate location where the surgical manipulation is being carried out.

In order to address these issues, various techniques have been considered. For example, in neurosurgery there is an optical surgical navigation apparatus disclosed in non patent document 1. This apparatus is configured such that correspondence in the same coordinate system are made between the surgical field and MRI images of the head captured prior to surgery using positions detected using infrared light. The position of the location currently being surgically manipulated is also detected, and the location currently being surgically manipulated is displayed on the MRI images.

There is also a navigation apparatus disclosed in non patent document 2. This apparatus is configured to capture ultrasound tomographic images during surgery using an ultrasound probe, and to detect the position of the ultrasound probe using infrared light. Correspondence is made of MRI images of the head captured prior to surgery with the ultrasound tomographic images captured during surgery, and the location currently being surgically manipulated is displayed on the MRI images, in a similar manner to the optical surgical navigation apparatus in non patent document 1.

Also a data recording technique is disclosed in patent document 1. In this technique a three-dimensional scanning unit is used, three-dimensional image data of the skin surface of a patient is acquired, and this is corresponded with, and displayable on, image information from MRI images and the like of the patient captured prior to surgery.

Non patent document 1: Medtronic SNT, "StealthStation", accessed online Sep. 2, 2005 at internet <URL:http//www.stealthstation.com/physician/neuro/library/treon.jsp>.

Non patent document 2: Medtronic SNT, "SonoNav", accessed online Sep. 2, 2005 at internet <URL:http//www.stealthstation.com/physician/neuro/library/sononay.jsp>.

Patent document 1: Japanese Patent Application Laid-Open (JP-A) No. 9-511430

DISCLOSURE OF THE INVENTION

Problem to be Solved by the Invention

However, the above-described navigation apparatuses are extremely expensive, and do not reduce the burden on the patient in use, since it is necessary to perform marking of the patient for the images captured prior to surgery (MRI etc.). In addition, since the position of the surgical instrument is detected by light from a specific direction, such as from around the feet of the patient, there are limited degrees of freedom in the usage direction of the surgical instrument, and the burden on the surgeon is increased.

Furthermore, since the above-described technique for data recording requires a special unit to be added for detecting the position of the surgical instrument, further correction of the coordinate system is required, and the device configuration becomes complicated and operation thereof also becomes difficult.

Also, in order to know during surgery the position of the surgical instrument and the position being manipulated, use of the above intraoperative CT/MRI could also be contemplated, however the problem is that this requires significant capital investment, such as in refurbishment of the operating room.

The present invention is made in the light of the above circumstances and an objective thereof is to provide a surgery support device capable of presenting images showing with high resolution the state of the surgical field during surgery realized with a simple structure, and a surgery support method, and surgical support program.

Method of Solving the Problem

In order to address the above issues, the invention of claim 1 is a surgery support device configured to include: a profile measurement means, optically measuring a surface of a subject and obtaining surface profile information representing the three-dimensional position of each location on the subject surface; input means, inputting plural high resolution tomographic images of the subject captured prior to surgery; correspondence processing means, acquiring the surface profile information obtained by the profile measurement means prior to surgery and corresponding each location on the subject surface with a surface position in the high resolution tomographic images, based on the acquired surface profile information and based on the plural high resolution tomographic images input by the input means; acquisition means, optically measuring an exposed portion of a surgical instrument having a specific profile used for surgery by using the profile measurement means during surgery, and acquiring instrument position information representing the three-dimensional position of an unexposed portion including the distal end portion of the surgical instrument, based on the measured position of the exposed portion; combining means, combining, based on the instrument position information acquired by the acquisition means, a surgical instrument image with the high resolution tomographic images such that the surgical instrument image showing the unexposed portion of the surgical instrument is aligned with each position of the unexposed portion including the distal end portion of the surgical instrument; and a display controller, displaying the combined high resolution tomographic images combined by the combining means on a display.

In the surgery support device according to the present invention, plural high resolution tomographic images (plural sections of an surgical field obtained at one time of tomographic image capture that have each been made into an image visible at high resolution) of the surgical field captured prior to surgery are used. It should be noted that a three-dimensional model of the surgical field generated based on plural high resolution tomographic images may also be used. The surgical field is also not limited to the head, and application can be made to a chosen part of a biological subject. It is preferable to use MRI images captured using Nuclear Magnetic Resonance-Computed Tomography (such MRI images including MRI images in which functional mapping showing a map of partitioning of each function has been overlaid on MRI images). However, tomographic images captured for example by X-ray CT imaging and the like, and by other known imaging methods may also be used, as long as these images are tomographic images that represent the surgical field with high resolution. As a three-dimensional model of the surgical field, for example, a three-dimensional model from amalgamating a large number of individual three-dimensional elements of the surgical field may be used. Such a three-dimensional model may be derived by extracting respective image regions corresponding to the surgical field from plural high resolution tomographic images, setting for the extracted image regions a large number of readily discriminated feature points positioned on the surface of the surgical field or positioned within the surgical field (for example points corresponding to the features of the bones and mucus membranes forming the surface of the face and the paranasal sinuses if the surgical field is the paranasal sinuses) and also deriving the three-dimensional coordinate of each of the feature points, and generating a biological model of the edges of the surgical field by partitioning into the large number of individual three-dimensional elements with each of the set feature points as apexes (nodes). Images of such a three-dimensional model projected onto a plane oriented in a specific direction may be used, and images of sections thereof taken along a specific direction may also be used.

Also, the profile measurement means optically measures the surface of the subject, such as the surface of the surgical field (for example the head or face surface) and obtains surface profile information representing the three-dimensional position of respective locations on the subject surface. An example of such a profile measurement means is, a profiling device using an light-section method for measuring the three-dimensional position by changes in position of a line of light beam on the subject when projecting the line of light onto the subject from a specific direction, a profiling device using a pattern projection method for measuring the three-dimensional position by projecting a lattice of lines of light onto the subject, and a profiling device using an optical scanning method measuring the three-dimensional position by scanning a light spot, such as a laser beam, in a specific direction. It should be noted that in the present invention the surface profile of the surgical field is measured prior to surgery in order to align with the plural high resolution tomographic images (referred to as registration, and to as corresponding, described later). However, during surgery the surgical field is covered with a sheet called a drape, and only a limited portion of the surgical field is exposed (for example the nose is exposed in paranasal sinus surgery). Consequently surface profile information is obtained prior to surgery. The input means inputs plural high resolution tomographic images of the subject captured prior to surgery. The correspondence processing means corresponds each location on the subject surface with a surface position in the high resolution tomographic images, based on the surface profile information acquired by the profile measurement means and based on the plural high resolution tomographic images input by the input means. Consequently marking of the patient prior to surgery and image capture thereof is not required.

The acquisition means optically measures the exposed portion of the surgical instrument having a specific profile used for surgery and acquires instrument position information representing the three-dimensional position of the unexposed portion (a portion not exposed during surgery, an inserted portion such as a portion within the surgical field, in a deep layer thereof or on the bottom surface thereof) including the distal end portion of the surgical instrument, based on the measured position of the exposed portion.

It should be noted that the acquisition means may optically measure the surface of the subject during surgery (for example the surface of the surgical field (a portion exposed during surgery)) and acquire the exposed positional information representing the three-dimensional position of each location on the surface. For example when there are slight movements or distortions of the subject generated due to manipulation during surgery (or displacement or distortion of the surgical field) the correspondence relationships, between each location of the subject surface and surface positions in the high resolution tomographic images, corresponded by the correspondence processing means, break down, leading to a decrease in precision of the high resolution tomographic images captured prior to surgery. In order to address this issue, since the three-dimensional position changes for each of the locations on the surface of the subject, represented by the exposed positional information acquired with the acquisition means at specific intervals in time, a correction means is provided for correcting the plural high resolution tomographic images for each location on the subject based on the changed exposed positional information, namely correcting the correspondence relationships between the each of the locations on the subject surface to the respective position on the surface in the high resolution tomographic images. By so doing, high resolution tomographic images can be obtained which represent with high resolution in the state of the subject after a slight movement or deformation.

The combining means combines the surgical instrument image with the high resolution tomographic images. Namely, the combining means combines the surgical instrument image onto the high resolution tomographic images such that the surgical instrument image showing the unexposed portion of the surgical instrument is aligned with each position of the unexposed portion including the distal end portion of the surgical instrument. The combined high resolution tomographic images are displayed on the display by the display controller, therefore images representing with good precision in the state of the surgical field during surgery can be presented to the surgeon, enabling a contribution towards an increase in surgical precision.

Since the surface profile information of each location on the subject surface is corresponded by the corresponding means with the plural high resolution tomographic images of the subject captured prior to surgery, there is no need to mark the patient prior to surgery and to capture images of the marks, therefore images are readily provided without troubling the patient, without using a frame and also without the need for marking. In addition, since the optical measurement of the subject surface by the acquisition means and the optical measurement of the surgical instrument can be performed with the acquisition means, the configuration is simplified and a much lower cost device can be realized, the surgery support device of the present invention having a greatly simplified device configuration in comparison to when MRI images are captured at regular intervals during surgery. Also, the optical measurements can be performed in a much shorter period of time in comparison to using any type of MRI imaging device, therefore according to the present invention, long periods of lost time during surgery in order to make the above measurements can be avoided.

The invention of claim 2 is the surgery support device of claim 1, in which the profile measurement means includes a scanning device that scans a laser beam on the surface of the subject, and detection means that detects the three-dimensional position of the location of irradiation of the laser beam on the subject surface by receiving light of a reflected laser beam from the subject surface, and the three-dimensional position detection by the detection means is carried out repeatedly while scanning the laser beam over each location on the subject surface. By so doing the surface profile information and the surgical instrument positional information may be acquired. The detection of the three-dimensional position using the detection means can be performed using, for example, a triangulation method.

Since, for example, the three-dimensional position of each location on the surface of the surgical field can be detected using a non-contact mode by the profile measurement means configured as described above, the three-dimensional position of each of the locations on the surface of the surgical field can be detected without adverse influence on the surgical field, and without generating displacement or deformation of the surgical field, in comparison with detection of the three-dimensional positions of each of the locations while contacting each of the locations on the surface of the surgical field. In addition, by using a common configuration for measuring the subject surface and for measuring the position of the surgical instrument, the profile measurement means is configurable with a single device used as a scanning device scanning a laser beam and used as the detection means receiving light from a laser beam, and the device configuration can therefore be simplified. Adjustment can also be completed by executing the procedure for adjusting the scanning range etc. of the laser beam by the scanning device a single time. The profile measurement means preferably uses the profile measurement device with a scanning method of claim 2 in order to reduce the measurement time.

It should be noted that the acquisition means may further include image capture means for capturing the surface of the subject. The correspondence processing means acquires the surface profile information from the profile measurement means. However, in order to estimate the position of each location on the subject surface, it is preferable to determine which portion of a three-dimensional subject corresponds to each location on the surface of the surgical field revealed in three-dimensional positions, using the surface profile information and to perform corresponding therebetween. Such corresponding can, for example, use features seen on the surface of the surgical field (for example features of the face, such as the eyes, nose and ears). As an example, in order to capture the surface of the surgical field, images captured by image capture means may be used effectively to obtain the features representing the surface of the surgical field. With regard to estimating the position of each location on the subject surface using such captured images, since corresponding may be performed based on images captured by the image capture means independently of the type etc. of the feature (for example the feature might be a feature which does not change along with the three-dimensional position, such as a change in color or the like), and consequently the precision of the correspondence relationships can be increased. It should be noted that the image capture means preferably is set with a common scanning device and detection means so that the image capture range matches the detection range of the three-dimensional position of each of the locations on the surface of the surgical field (for example the scanning range of a laser beam with the scanning device). By so doing, it becomes unnecessary to perform corresponding of the images captured by the image capture means and the surface profile information, and corresponding of the surface profile information is readily performed.

The acquisition means can estimated the three-dimensional position of the unexposed portion including the distal end portion of the surgical instrument, based on predetermined data corresponding to plural locations on the measured exposed portion with the specific profile.

The surgical instrument used in surgery is an instrument having a specific profile that has been determined in advance. Consequently the dimensions, purpose of use, method of use etc. thereof that are known. By recording in advance data corresponding to these factors, there is no need to provide a new means for determining the three-dimensional position of the surgical instrument as a whole, and the device configuration can be simplified even further.

The combining means derives a predicted position for when the distal end portion of the surgical instrument is moved within a predetermined movement range, based on the instrument position information acquired by the acquisition means. The combining means is also able to combine the high resolution tomographic images with the surgical instrument image, as a predicted position image, such that the surgical instrument image showing the distal end portion of the surgical instrument is positioned at plural positions from the position of the distal end portion of the surgical instrument prior to movement up to the predicted position thereof, or up to an intervening position towards the predicted position.

Also, the combining means derives a predicted position for when the distal end portion of the surgical instrument is moved within a predetermined movement range, based on the instrument position information acquired by the acquisition means, and is able to further combine the high resolution tomographic images with the surgical instrument image as a predicted position image such that the surgical instrument image showing the distal end portion of the surgical instrument is positioned at plural positions from the position of the distal end portion of the surgical instrument prior to movement up to the predicted position thereof, or up to an intervening position towards the predicted position.

However, there are occasions during surgery when, depending on the progress of surgery, investigation is undertaken into how far the distal end portion of the surgical instrument should be moved (forward). In such cases effective information presentation is made to the surgeon etc. by showing which position would be reached if the surgical instrument was moved by however much from the current position. The predicted position is derived for when the distal end portion of the surgical instrument is moved within a predetermined movement range, based on the instrument position information acquired by the acquisition means. Then plural positions from the position of the distal end portion of the surgical instrument prior to movement up to the predicted position thereof, or at plural intervening positions up to the predicted position, are derived. Such plural positions may be intermittent positions each at a specific interval apart, or these may be continuous positions. Further combination is made with the surgical instrument image as a predicted position image on the high resolution tomographic images, such that the surgical instrument image shows the distal end portion of the surgical instrument positioned in such plural positions. Such combined images may be superimposed with the surgical instrument image positioned in plural positions, or separate combined images may be generated for each position and these plural images output in sequence. By so doing, the surgeon etc. is readily shown which position the distal end portion of the surgical instrument would reach in the surgical field if the surgical instrument was moved from the current position.

A surgery support method according to another invention, in a similar manner to the surgery support device of the present invention, presentation of images showing with good precision the state of the surgical field during surgery is realized with a simple device configuration. The surgery support method, in more detail, is a surgery support method supporting surgery by displaying, on a surgery support system provided with a display for displaying high resolution tomographic images, a surgical instrument on the high resolution tomographic images at the same time that the high resolution tomographic images are being displayed on the display during surgery, the surgery support method including: a step in which the surface of a subject is optically measured and surface profile information representing the three-dimensional position of each location on the subject surface is obtained; a step in which a plural high resolution tomographic images of the subject captured prior to surgery are input; a step in which the surface profile information obtained by the profile measurement means prior to surgery is acquired and each location on the subject surface is corresponded with a surface position in the high resolution tomographic images, based on the acquired surface profile information and based on the plural high resolution tomographic images input by the input means; a step in which during surgery an exposed portion of a surgical instrument having a specific profile used for surgery is optically measured, and instrument position information representing the three-dimensional position of an unexposed portion including the distal end portion of the surgical instrument is acquired, based on the measured position of the exposed portion; a step in which a surgical instrument image is combined, based on the acquired instrument position information, with the high resolution tomographic images such that the surgical instrument image showing the unexposed portion of the surgical instrument is aligned with each position of the unexposed portion including the distal end portion of the surgical instrument; and a step in which the combined high resolution tomographic images combined by the combining means are displayed on a display.

It should be noted that in the present invention each location on the subject surface is corresponded with a surface position in the high resolution tomographic images, and this correspondence acts as the base. During surgery, the instrument position information of the surgical instrument used in surgery is acquired, and the surgical instrument image is combined with respective plural high resolution tomographic images. Generally during surgery, the surgical field is covered by a sheet called a drape, and it is often difficult to perform measurements using a profile measurement means. However, the above corresponding may be repeated while profile measurement of an extremely limited portion (for example, in paranasal sinus surgery the nose is exposed) is carried out. In addition, the surgical field may be readily exposed just by peeling off the sheet called a drape. Consequently re-alignment (registration) may be carried out by optical measurement of specific exposable structures of the face, for example the nose, ears etc.

Also a surgery support program according to another invention causes a computer to function as the surgery support device when executed in the computer, with presentation of images showing with good precision in the state of the surgical field during surgery realized with a simple configuration. The surgery support program, in more detail, is executed in a surgery support system provided with a computer connected to a display for displaying high resolution tomographic images, the surgery support program displaying a surgical instrument on the high resolution tomographic images at the same time that the high resolution tomographic images are being displayed on the display during surgery, the surgery support program causing the computer to execute processing including: a step in which the surface of a subject is optically measured and surface profile information representing the three-dimensional position of each location on the subject surface is obtained; a step in which a plural high resolution tomographic images of the subject captured prior to surgery are input; a step in which the surface profile information obtained by the profile measurement means prior to surgery is acquired and each location on the subject surface is corresponded with a surface position in the high resolution tomographic images, based on the acquired surface profile information and based on the plural high resolution tomographic images input by the input means; a step in which during surgery an exposed portion of a surgical instrument having a specific profile used for surgery is optically measured, and instrument position information representing the three-dimensional position of an unexposed portion including the distal end portion of the surgical instrument is acquired, based on the measured position of the exposed portion; a step in which a surgical instrument image is combined, based on the acquired instrument position information, with the high resolution tomographic images such that the surgical instrument image showing the unexposed portion of the surgical instrument is aligned with each position of the unexposed portion including the distal end portion of the surgical instrument; and a step in which the combined high resolution tomographic images combined by the combining means are displayed on a display.

Effect of the Invention

As has been explained above, the present invention uses a correspondence processing means to correspond the surface profile information of each location on the surface of the subject with the plural high resolution tomographic images captured prior to surgery, using correspondence processing not on a point basis but with the surface profile as the object of processing. Consequently, there are the superior effects of not only it being not necessary to mark the patient prior to surgery and not necessary to image the marks, but there is no burden on the patient, and, for example, a frame used for acquiring the three-dimensional coordinates used in stereotactic neurosurgery is not required, and images are readily presented. In addition, optical measurement of the subject surface, and optical measurement of the surgical instrument can be performed using the profile measurement device, realizing a simply configured device that may dramatically reduced cost.

BRIEF DESCRIPTION OF THE DRAWINGS

FIG. 5C is an image related to MRI imaging, showing MRI images and a generated model.

BEST MODE OF IMPLEMENTING THE INVENTION

Explanation will be given below of details of one example of an exemplary embodiment of the present invention, with reference to the drawings. In the explanation of the present invention below an example is given to an application in which to support surgery of a patient's head (in particular the face, paranasal sinuses and the like), however the present invention is not limited thereto.

Figure 1:
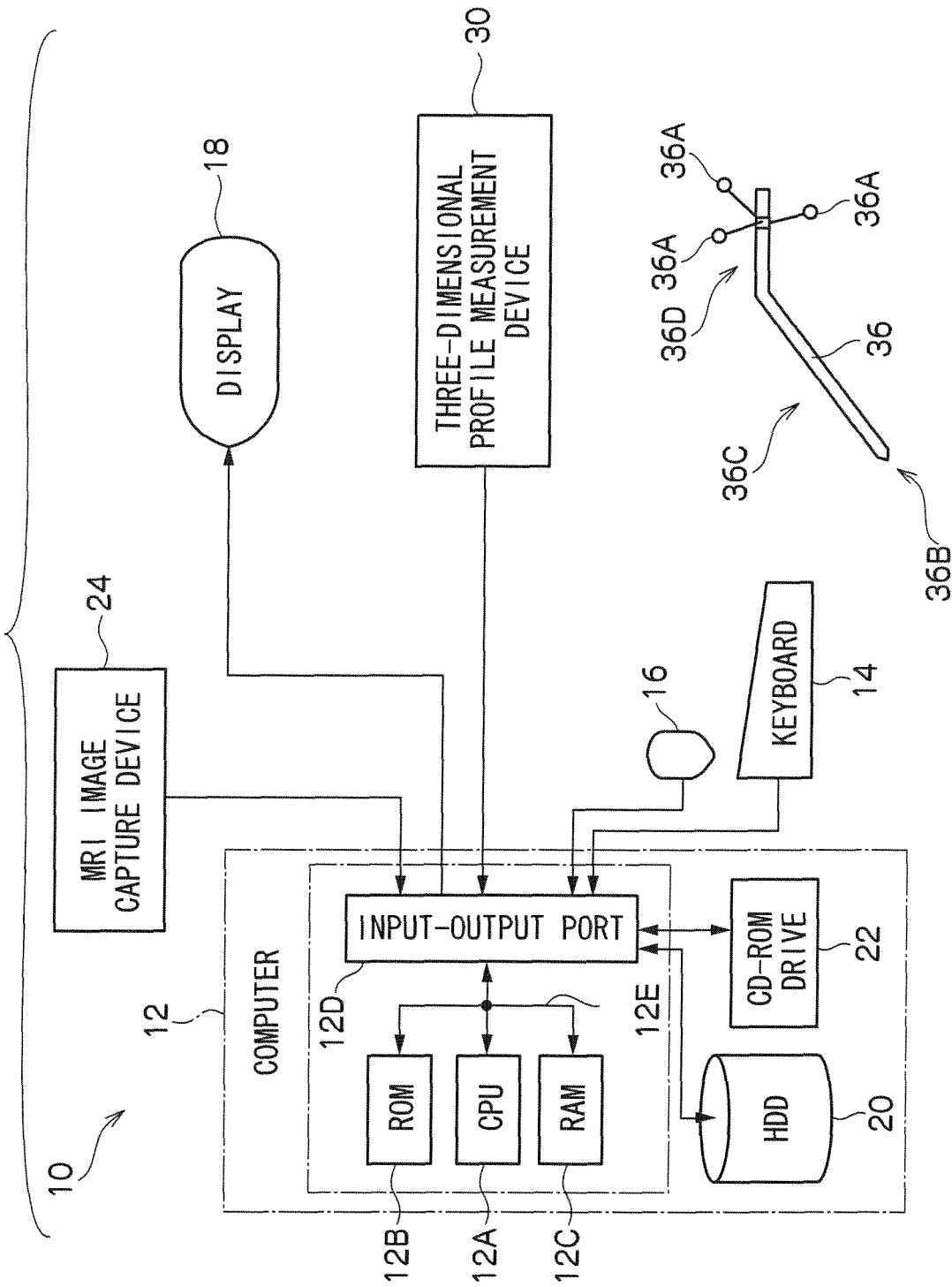
FIG. 1 is a block diagram showing a schematic configuration of a surgery support device.

A surgery support device 10 according to the present exemplary embodiment is shown in FIG. 1. The surgery support device 10 is provided with a computer 12, configured such as by a personal computer (PC). The computer 12 is provided with a CPU 12A, a ROM 12B, a RAM 12C, and an input-output port 12D, with these being mutually connected together through a bus 12E. Connected to the input-output port 12D are: a keyboard 14 and a mouse 16, for a user to input various information and to give various instructions; a display 18, configured from a LCD or a CRT and capable of displaying given information thereon; a hard disk drive (HDD) 20; and a CD-ROM drive 22. The display 18 corresponds to the display means according to the present invention. The surgery support device 10 corresponds to the surgery support device of claim 1, and to the surgery support system of claim 7 and claim 8.

A surgical navigation program, such as a three-dimensional model generation program for generating a later described three-dimensional model and an MRI image display program for performing later described MRI image display processing, is pre-installed on the HDD 20 of the computer 12. In the present invention, the computer 12 corresponds to the computer recited in claim 8, and the surgical navigation program corresponds to the surgery support program according to the invention recited in claim 8. The computer 12 has the capability of functioning as the surgery support device recited in claim 2 by executing the surgical navigation program.

There are a number of ways in which the surgical navigation program can be installed on the computer 12. For example, the surgical navigation program may be installed by recording the surgical navigation program in the setup program and on a CD-ROM, the CD-ROM set in the CD-ROM drive 22 of the computer 12, and the surgical navigation program read out from the CD-ROM and written sequentially onto the HDD 20 when execution of the surgical navigation program is instructed to the CPU 12A, and various settings performed according to the requirements.

There is an MRI image capture device 24, capable of capturing high resolution tomographic images (MRI images) of a body along a given direction using Nuclear Magnetic Resonance-Computed Tomography, and also a three-dimensional profile measurement device 30, each connected to the input-output port 12D of the computer 12. It should be noted that video camera(s) (for example 3 thereof) may be connected to the input-output port 12D. Such video camera(s) are not essential elements in the configuration of the present invention, and may be used when the need arises, and video camera(s) outputting a black and white image or a color image signal may be used. The MRI image capture device 24 corresponds to the image capture device that captures "plural high resolution tomographic images of the surgical field" prior to surgery, and is placed in an MRI imaging room, a different room to the operating room where the surgery is operated. It should be noted that the MRI image data captured by the MRI image capture device 24 prior to surgery may be acquired when the computer 12 executes the later described MRI image display processing. It is therefore not essential for the MRI image capture device 24 to be connected to the computer 12, and the MRI image data may be transferred from the MRI image capture device 24 to the computer 12 via a compatible read-out device for any one of various types of recording media, such as, for example, a CD-R, and CD-RW, MO, ZIP, DVD-R, DVD-RW or the like. Consequently the input-output port 12D, which acquires the MRI image data from the MRI image capture device 24 and from read-out devices for various recording media, corresponds to the input means of the present invention.

A surgical instrument 36 used by the surgeon during surgery is shown in FIG. 1. This surgical instrument 36 is a bar shaped instrument, configured with: a unexposed side 36C, including a distal end portion 36B, formed from a unexposed portion for contact with, and insertion into, the target object (the surgical field) of the field of operation; and an exposed side 36D, formed from an exposed portion for holding by the surgeon etc. There are a specific number of spheres 36A of a given diameter (for example 5 mm) attached by arms to the exposed side 36D. These spheres 36A are detection references for determining each position of the surgical instrument 36. The shape of the surgical instrument 36 is measured in advance, and the positional relationship of the spheres 36A to the surgical instrument 36 are also measured in advance. This measurement data is stored in advance on the HDD 20. A modified example of the surgical instrument is an endoscope with an inserted fiber for viewing the unexposed portion of the surgical field. An endoscope is principally configured with an adjustment mechanism, for adjusting the magnification and the bend angle of the distal end portion, and a fiber (omitted in the figures). The shape of such an endoscope is measured in advance, and the deformation amount and positional relationship of the endoscope to the adjustment mechanism (not illustrated) is measured in advance. Then in a similar manner to with the surgical instrument 36, the positional relationships and moving relationships of the endoscope can be identified by providing the above-described spheres to the endoscope for determining the position thereof, together with inputting adjustment amounts to the adjustment mechanism so as to cause deformations. This measurement data may be stored on the HDD 20. Explanation is given below in which spheres are provided to the surgical instrument 36, however, there is no limitation thereto, and for example the shape of the surgical instrument 36 may be measured in detail in advance, and the location of features on the surgical instrument 36 may be used, corresponding to such spheres.

With respect to this, in the present exemplary embodiment the three-dimensional profile measurement device 30 is provided in the surgery support device 10, however the three-dimensional profile measurement device 30 may measure (three-dimensional profile measurements of) different subjects at the same time, and the position of the surgical instrument may be detected during the operation along with carrying out measurements of the shape of the face etc. of the patient.

Figure 3A:
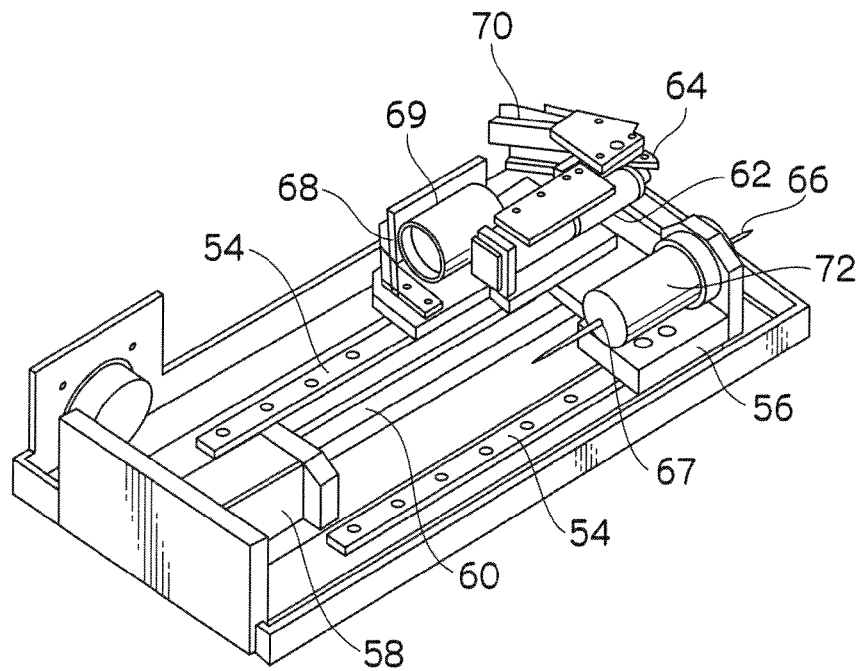
FIG. 3A is a perspective view showing the internal configuration of a three-dimensional profile measurement device in a given sub-scanning position.
Figure 3B:
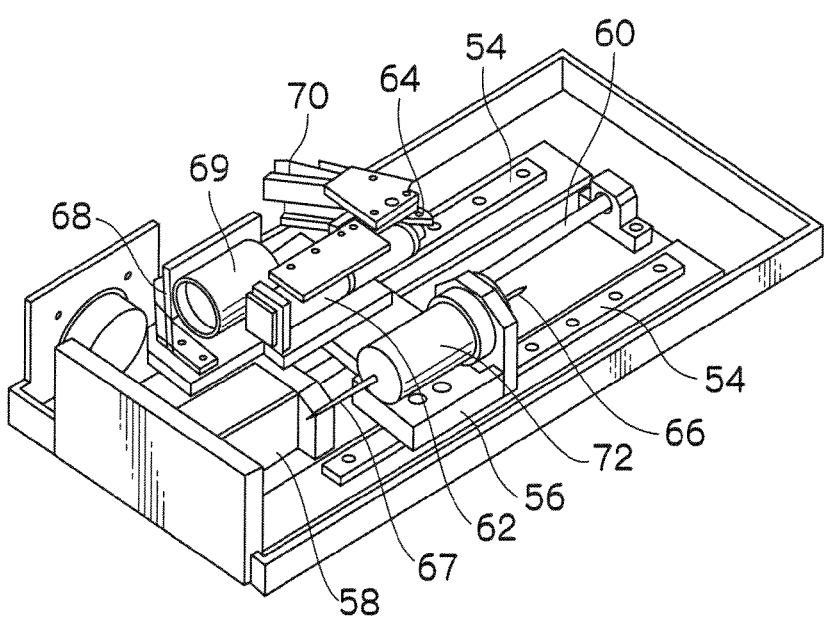
FIG. 3B is a perspective view showing the internal configuration of the three-dimensional profile measurement device in a different sub-scanning position to that shown in 3A.

The three-dimensional profile measurement device 30, as shown in FIGS. 3A and 3B, is provided with a moveable base 56 that spans across between a pair of rails 54. The moveable base 56 is mounted meshed with the thread of a ball screw 60, which extends parallel to the rails 54 and is rotated by a motor 58. The moveable base 56 slides along the rails 54 with the rotation of the ball screw 60. Disposed in sequence at the laser beam (send-laser beam) emission side there are a light emitting unit 62, configured to include a laser beam source and attached to the moveable base 56, and a mirror 64, mounted to the moveable base 56, followed by a mirror galvanometer 66, whose facing is changed by the driving of a motor 72. The send-laser beam emitted from the light emitting unit 62 is reflected by the mirror 64 and the galvanometer mirror 66 and emitted from the housing.

The send-laser beam emitted from the housing of the three-dimensional profile measurement device 30 is reflected by an irradiated body (for example the surface of the brain as the surgical field), and returns as a return laser beam, passing through a cover 50 and being incident on a mirror 67. The mirror 67 is also attached to the rotational axis of the motor 72, facing in the same direction as the mirror galvanometer 66, and is configured such that the facing direction of the mirror 67 is changed by driving the motor 72. A mirror 68, a lens 69 and a line sensor 70, made up from plural photoelectric converter elements, are disposed in sequence in a row on the return-laser emission side of the mirror 67. The return-laser incident on the mirror 67 is reflected by the mirrors 67 and 68, passes through the lens 69 and is received as light by the line sensor 70. An output signal from the line sensor 70 is input to the controller of the three-dimensional profile measurement device 30 through an amplifier and an A/D converter (these components are omitted in the drawings). A position sensor for detecting the position of the moveable base 56 and an angle sensor for detecting the facing direction of the mirror galvanometer 66 (and mirror 67) are also connected to the controller.

The controller determines, based on the light reception data, input from the line sensor 70 through the amplifier and A/D converter, whether the laser beam has been received by any of the photoelectric converter elements in the line sensor 70. The controller then determines (computes) using a triangulation method the three-dimensional coordinates of the laser beam reflection position on the irradiated body (to be precise three-dimensional coordinate in a three-dimensional system with the position of the housing of the three-dimensional profile measurement device 30 as the reference (referred to as a housing-based coordinate system)), based on the position of the photoelectric converter element(s) in the line sensor 70 where the laser beam has been received and based on the position of the moveable base 56 and the facing direction mirror galvanometer 66 detected by the sensors. Each of the motors 72 and 58 are also connected to the controller, and the incident position of the laser beam on the irradiated body is moved (primary scanning) along a direction orthogonal to the axial direction of the rotation axis of the motor 72 by driving the motor 72 and changing the facing direction of the mirror galvanometer 66 (and the mirror 67). The incident position of the laser beam on the irradiated body is also moved (secondary scanning) along a direction parallel to the rails 54 by driving the motor 58 and moving the moveable base 56.

The surface profile of the irradiated body (three-dimensional coordinates for each of the positions on the surface of the irradiated body) is measured by the three-dimensional profile measurement device 30 across the entire surface of the irradiated body. The three-dimensional profile measurement device 30 carries out the measurement of the surface profile of the irradiated body when instructed from the computer 12, and data obtained from the measurement, representing the three-dimensional coordinates of each position on the surface of the irradiated body (this data is referred to below as surface measurement data) is output to the computer 12. It should be noted that surface measurement data corresponds to surface profile information, and the rails 54, the moveable base 56, the motor 58, the ball screw 60, the light emitting unit 62, the mirror 64, the mirror galvanometer 66, and the motor 72 correspond to the scanning device of claim 2, the with the mirror 67, the mirror 68, the lens 69 and line sensor 70, the and motor 72 corresponding respectively to the detection means of claim 2. When the video camera(s) are provided, the position and facing directions thereof are preferably adjusted such that the video camera(s) capture images from the same range as the measurement range of the three-dimensional profile measurement device 30. In addition, the measurement range of the three-dimensional profile measurement device 30 should be set to include at least the entire region of the face of the subject patient (preferably the entire region of the head), and the operational range within which the surgeon manipulates the surgical instrument 36 should be set to fall within the encompassed three-dimensional region set in advance.

Figure 2:
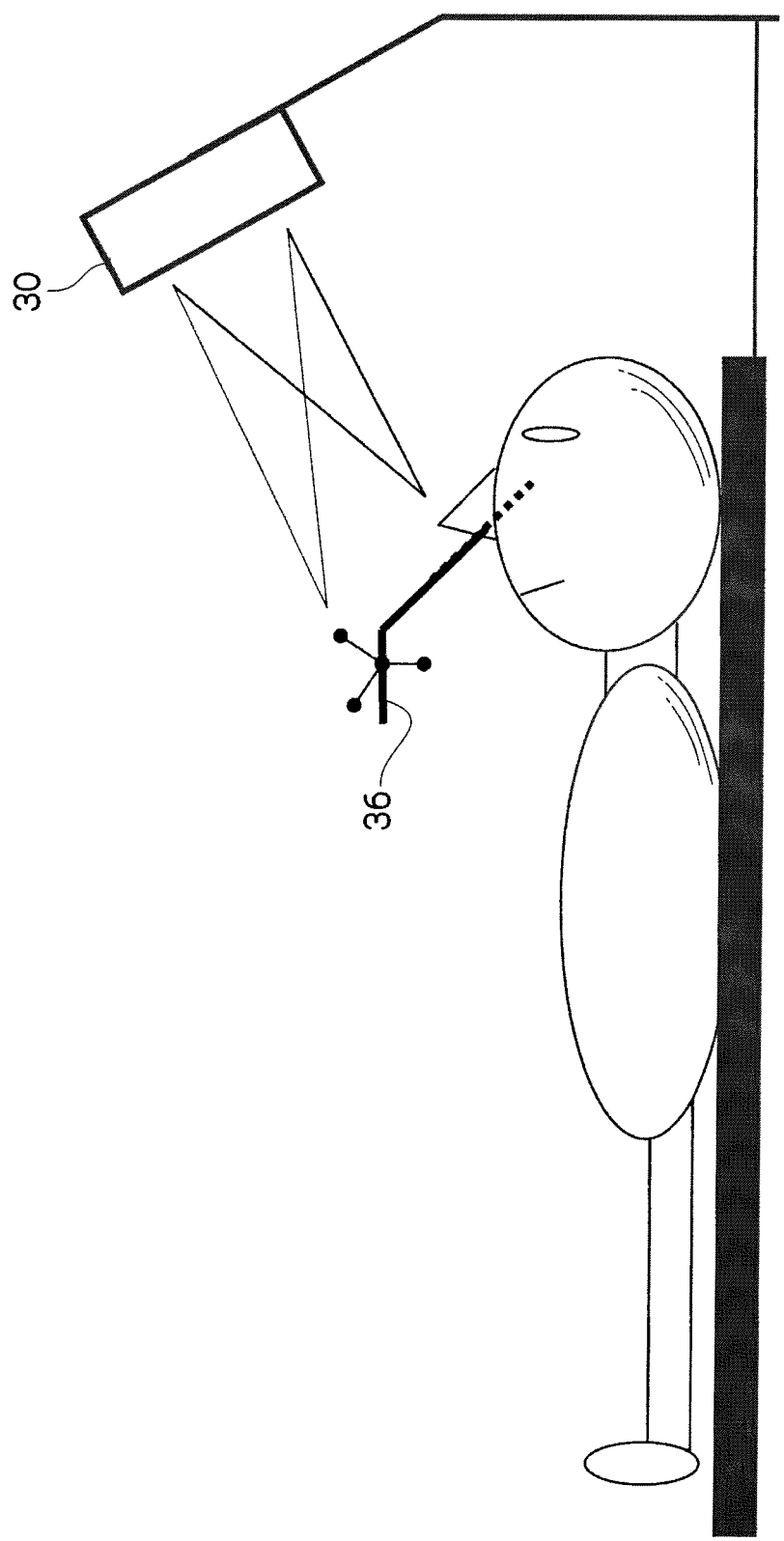
FIG. 2 is a schematic diagram of a case in which a three-dimensional profile measurement device is provided independently.

It is preferable that, as shown in FIG. 2, the three-dimensional profile measurement device 30 has a measurement range set such that the entire region of the face of the subject patient is included therein, and also that the operational range within which the surgeon manipulates the surgical instrument 36 is set so as to include the encompassed three-dimensional region. When so doing, it is preferable that, as an example of a position in which the patient does not impede the surgical operation, a position above and at an angle to the subject patient (to the top right in FIG. 2) near to the surgical field is set for carrying out scanning. In this manner, the shape of the head or face of the subject patient is detected, and measurements are made of the three-dimensional coordinates for each position thereon. When this is undertaken, the three-dimensional coordinates are measured of the spheres 36A that are attached to the surgical instrument 36 and formed from a highly reflective material. It should be noted that when the shape of the surgical instrument 36 is measured in advance and the location of features on the surgical instrument 36 that are used in place of the spheres, the location of features corresponding to the spheres are detected by image processing based on the shape of the surgical instrument obtained by scanning the surgical instrument 36 with the three-dimensional profile measurement device 30. The three-dimensional coordinates of these determined locations may be used as the three-dimensional positions of the spheres 36A.

FIG. 2 shows an example of surgery to the paranasal sinuses, and a sheet called a drape that covers the patient during surgery and through which the nose is exposed is omitted in the figure. In addition the position of the patient may be changed by fixing the three-dimensional profile measurement device 30 to the operating table and by rotating the operating table, and with such a configuration later described registration need only be undertaken once initially, since the position of the three-dimensional profile measurement device 30 to the patient does not change.

Explanation will now be given of the operation of the present exemplary embodiment. In the present exemplary embodiment, when performing surgery related to paranasal sinuses in the field of ENT, first MRI images of the head of the patient (subject patient) are captured in advance using the MRI image capture device 24. It should be noted that it is not necessary to make the pre-surgery marks formed from a material that shows up in the MRI images. This is because, as will be described later, the feature locations and shape of the patient (for example the reference points 81 which are at the apex of both ears and the nose of the patient shown in FIG. 5B) are determined from of each of the positions measured by the three-dimensional profile measurement device 30.

Figure 5A:
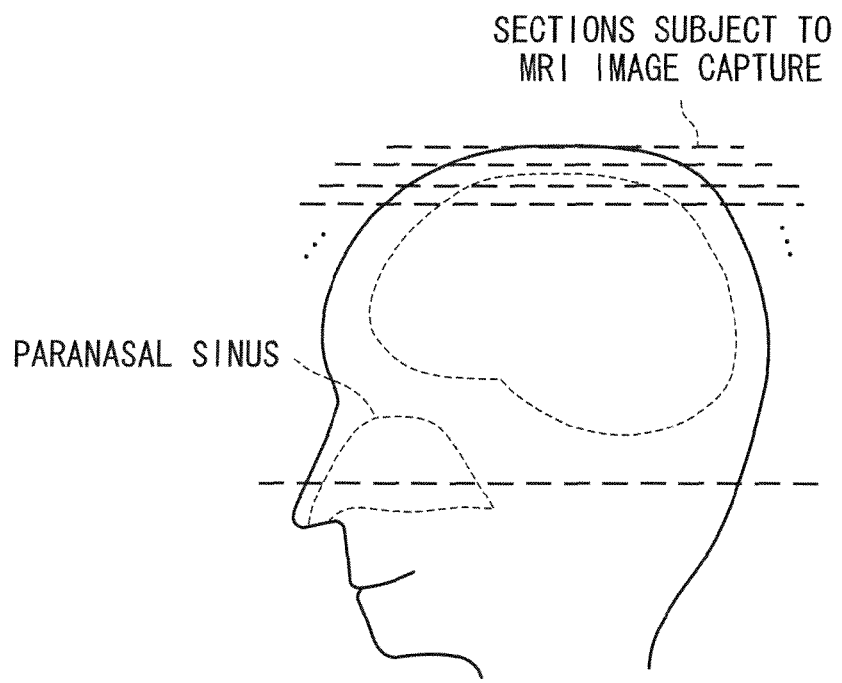
FIG. 5A is an image related to MRI imaging, showing imaging sections during image capture.
Figure 5B:
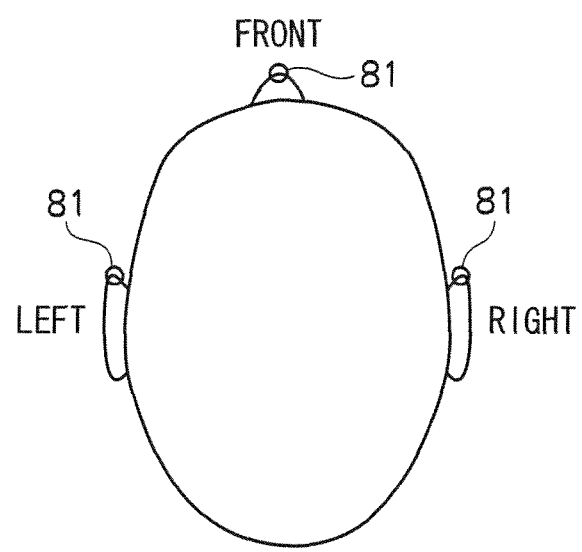
FIG. 5B is an image related to MRI imaging, showing head reference points when in a recumbent position.

An example of MRI images is, as shown in FIG. 5A, images captured by the MRI image capture device 24 at each of plural sections of the head of the patient, set at a uniform separation (for example about 1 mm). It should be noted that while marks are not required during image capture as stated above, the image capturing includes the ears, nose, mouth and eyes in order to identify various positions for recognition of the surface profile. Plural MRI images (high resolution tomographic images of the surgical field) are thereby obtained, which make visible at high resolution each of the sections set. It should be noted that the boundary lines between the patient's skin to the air is included in each of the plural MRI images obtained by image capture, and the surface profile of the patient can be obtained from these boundary lines. The plural MRI images obtained by the MRI image capture device 24 correspond to the plural high resolution tomographic images (MRI images) of the present invention.

The data of the plural MRI images obtained as described above is input to the computer 12 from the MRI image capture device 24, and stored on the HDD 20. Generation of a three-dimensional model of the surface profile is then performed by the computer 12, as a three-dimensional biological model of the patient for use in registration of the patient (detailed later).

Figure 4:
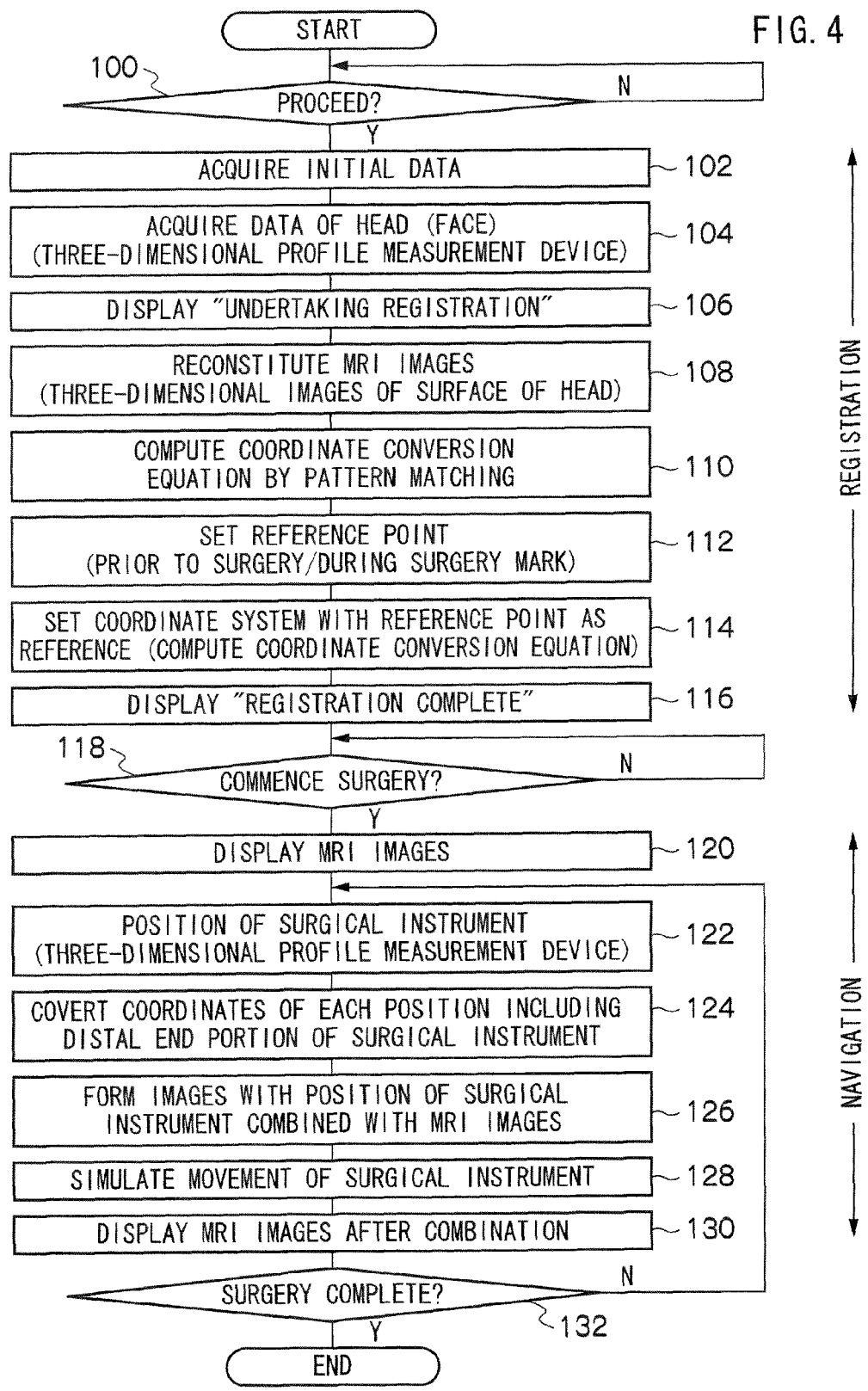
FIG. 4 is a flow chart showing the contents of MRI image display processing executed in a computer of a surgery support device.

In the present exemplary embodiment, during surgery surgical navigation processing, including MRI image display processing, is executed by the computer 12 when instruction to start up the surgical navigation program is made by the surgeon as the surgery progresses. Such surgical navigation processing including MRI image display processing is shown in the flow chart of FIG. 4 and will be explained below.

First, the patient is placed in a specific position (for example a recumbent position), and the head, which is the surgical field, is firmly restrained. The three-dimensional profile measurement device 30 is also fixed in a specific position (such as a position that does not impede surgical operation above the surgical field). When such fixing is completed, information indicating that the surgery is proceeding is input by the surgeon through the keyboard 14, and the routine proceeds to step 100. Negative determination, i.e. not to start up the surgical navigation program, is made at step 100 up to the point when instruction is given by the keyboard 14 to start the surgical navigation program. The routine proceeds to step 102 when this instruction is made. Various types of initial data are acquired at step 102. This initial data is such data as the data of the plural MRI images, data of the positional relationship of the three-dimensional profile measurement device 30, measurement data of the surgical instrument 36, etc. Registration is performed in the processing from step 102 up to step 116, including calibration processing that derives the coordinate conversion equation for converting coordinate values in the housing-based coordinate system during surgery to coordinate values in the MRI coordinate system. This registration is processing to align positions on the surface profile of the face of the patient from the MRI images to positions on the surface profile measured with the three-dimensional profile measurement device 30.

Next, at step 104, measurement of the surface profile is instructed to the three-dimensional profile measurement device 30. By so doing, measurements are made of the surface profile of the face of the patient (the three-dimensional coordinates of each location on the face) by the three-dimensional profile measurement device 30 emitting the send-laser beam toward the head of the patient, to include toward the surface of the face of the patient, and repeatedly detecting (computing) the three-dimensional coordinates of the irradiation position of the laser beam, based on the position on the line sensor 70 at which light from the return-laser is received after reflection from the head of the patient, while varying the facing direction of the mirror galvanometer 66 (and the mirror 67) and while moving the moveable base 56. The surface measurement data, output as measurement results for the surface profile by the three-dimensional profile measurement device 30, is data of three-dimensional coordinate values in the housing-based coordinate system. When measurement of the surface profile by the three-dimensional profile measurement device 30 is complete, a message indicating "undertaking registration" is displayed on the display 18 at step 106. This display indicates that the current state is one in which processing is being executed for aligning positions of the surface profile of the head of the patient from the MRI images with the positions on the surface profile measured by the three-dimensional profile measurement device 30.

Next, at step 108, using the plural MRI images, a three-dimensional biological model (three-dimensional model of the surface profile) is generated by reconstituting the MRI images. Explanation will now be given of the generation of this three-dimensional model of the surface profile. Reference points are first extracted from the plural MRI images represented by the input data. Such reference points may be apexes on the surface and points on the limbs of the patient, specific examples being the position of the apex of the nose, the highest point of the ears, the edge of the mouth, the center of the eyeball etc. These reference points are extracted by image processing that detects within the plural MRI images the most peripheral point of the boundary lines between the skin of the patient and the air in the MRI images, determines the features of the curved surface profiles of the nose, ears, mouth, eyeball etc. by joining the boundary lines of the plural MRI images, and detects the apexes of these determined features, thereby extracting the surface of the face.

One of the extracted points is next set as the origin of the three-dimensional coordinate system (referred to below as the MRI coordinate system). The respective image regions (namely the boundary lines) corresponding to the surface of the patient are extracted from the plural MRI images, and a number of easily discriminated feature points (points corresponding to the features of the face, and the nose, ear, mouth and eyeball etc.) are set for the respective image regions extracted from the plural MRI images, and the three-dimensional coordinates for the respective feature points are derived in the MRI coordinate system. The three-dimensional coordinates of the respective feature points in the MRI coordinate system and the position of the respective feature points on the MRI images are also stored, such as in the HDD 20.

A three-dimensional model representing the peripheral edge of the head of the patient (a three-dimensional model of the surface profile) is generated by connecting with edges the feature points (nodes) of positions on the surface of the patient from the plural feature points set above, and by taking the portions surrounded by the edges to be flat planes. There is a three-dimensional model representing the surface of the head of the patient shown in FIG. 5C (at the right side of the sheet). This three-dimensional model, which is a three-dimensional model of the surface profile, can be made by dividing the plural MRI images of the head of the patient into a large number of individual three-dimensional elements, and amalgamating the large number of individual three-dimensional elements to show the surface profile of the head of the patient. The computer 12 can also investigate the sparseness/density of the line points in the three-dimensional model of the surface profile, based on the three-dimensional coordinates of each of the feature points (each line point) in the MRI coordinate system. When regions exist in which the separation between the line points in the three-dimensional model of the surface profile is large (the density is low), additional line points can be added to these regions, and consequently a three-dimensional model of the surface profile can be configured with a uniform size for each of the three-dimensional elements. The computer 12 then stores the data for the generated three-dimensional model of the surface profile in the HDD 20.

The generation of the three-dimensional biological model, the three-dimensional model of the surface profile, described above may be undertaken in a separate computer, separated form computer 12, and the generated three-dimensional model of the surface profile transferred to the computer 12. Also, when there is a finished three-dimensional model of the surface profile that has been generated before, the processing of step 108 described above may be simply reading out the data from the finished generated three-dimensional model which is stored on a medium.

It should be noted that in the present exemplary embodiment the three-dimensional model of the surface profile may be generated for use in surface profile alignment of positions, described in detail later, however, other three-dimensional biological models that may be used include models made of organs and portions of organs, such as a three-dimensional model of the paranasal sinuses, a three-dimensional model of the brain etc. An example thereof is setting feature points for the surface of the head and internal portions thereof, and carrying out model generation for internal organs of the head of the patient by deriving three-dimensional coordinates of the respective feature points in the MRI coordinate system. For example, in the case of a three-dimensional model of the paranasal sinuses, image regions corresponding to the paranasal sinuses of the patient are respectively extracted from the plural MRI images. For each of the image regions extracted from the plural MRI images, the surface of the head or the internal portions thereof are located, a large number of feature points are set which are easily identified in the MRI images and in the surface measurement data, images, and the three-dimensional coordinates of each of the feature points are derived in the MRI coordinate system. The three-dimensional coordinates in the MRI coordinate system of each of the feature points and the positions of each of the feature points on the MRI images are also stored in the HDD 20 or the like. In the case of a three-dimensional model of the brain, image regions corresponding to the brain of the patient are respectively extracted from the plural MRI images. For each of the image regions extracted from the MRI images, the surface of the brain or the internal portions thereof are located, a large number of feature points are set which are easily identified in the MRI images and in the surface measurement data and ultrasound tomographic images (including points corresponding to the features of the brain such as the cerebral sulci and the convolutions of the brain, the arteries and veins etc., and including points corresponding to the boundaries of brain tumors and normal portions thereof) and the three-dimensional coordinates of each of the feature points are derived in the MRI coordinate system, and the three-dimensional coordinates in the MRI coordinate system of each of the feature points and the positions of each of the feature points on the MRI images, are stored in the HDD 20 or the like.

When reconstitution of the three-dimensional model of the surface profile (three-dimensional biological model) is complete, the routine proceeds to step 110, and after determining the feature locations on the face, the conversion equation is derived for combining surface profile data from the three-dimensional profile measurement device 30 by pattern matching. At step 108, the three-dimensional model of the reconstituted surface profile can be defined by three-dimensional coordinate values in the MRI coordinate system and surface positions thereof. However, the surface measurement data acquired at step 104 by the three-dimensional profile measurement device 30 is three-dimensional coordinate values in the housing-based coordinate system, and the surface positions thereof can be defined. The coordinate axes in the MRI coordinate system or the housing-based coordinate system are then moved and rotated so that the surface positions of the reconstituted three-dimensional model of the surface profile aligns with the positions of the surface measurement data acquired by the three-dimensional profile measurement device 30 at step 104 (such that differences in position are as small as possible). The determinants to move and/or rotate the axial coordinates of the coordinate system become parameters for the conversion equation between the MRI coordinate system and the housing-based coordinate system. By such pattern matching the features of the face, including the ears, nose, mouth, eyes etc., are corresponded. By computing the determinants for moving and/or rotating the axial coordinates in order to carry out such correspondence, the coordinate conversion equation for converting three-dimensional coordinate values between three-dimensional coordinate values in the housing-based coordinate system and three-dimensional coordinate values in the MRI coordinate system prior to surgery is derived, and the derived coordinate conversion equation is stored in the HDD 20.

Next, at step 112, one of the points within the pattern matched three-dimensional model of the surface profile is set as the navigation origin. Such setting may be carried out by the surgeon, or one or other of the points extracted as described above may be selected automatically. Then in step 114, a coordinate system is set with the set navigation origin as the origin of the coordinate axes. Namely, a coordinate conversion equation is derived for converting three-dimensional coordinate values from the three-dimensional coordinate values in the MRI coordinate system prior to surgery into a coordinate system with the coordinate axes origin of the set navigation origin, and the derived coordinate conversion equation is stored in the HDD 20. By setting the navigation origin in this manner x=0, y=0, z=0) there is no need to undertake registration as long as the positional relationship between the head and the image acquisition device during surgery does not change. Namely, it is possible to represent spatial information from the navigation origin (x coordinate, y coordinate, z coordinate) perspective, such that the position on the MRI images which corresponds to the position of the surgical field etc. can be shown. By carrying out the above the calibration processing is completed. Next, in step 116, a message indicating "registration complete" is displayed on the display 18.

Explanation has been given above regarding the surface profile where pattern matching is carried out so to give point-to-point correspondence of the MRI coordinates system and the housing-based coordinate system. However, it should be noted that a profile measurement model may be generated of the surface profile of the face in the housing-based coordinate system, from the surface measurement data from the three-dimensional profile measurement device 30, and pattern matching may be carried out for the whole of the surface profile. Such a profile measurement model can be generated in a similar manner to the three-dimensional model of the surface profile.

The registration prior to surgery is thereby complete. Namely, after fixing the patient and taking the position of the body prior to commencing surgery (before the sheet (drape) for surgery is used to cover the patient), the three-dimensional profile measurement device 30 is fixed in a location that does not impede surgical operation on the surgical field, the face surface, including the ears, nose, mouth, eyes etc., is scanned/measured, and this positional information (three-dimensional coordinate values) are corresponded to positions on the surface of the head in the reconstituted MRI images. One of the points therefrom is taken as the origin (x=0, y=0, z=0). The correspondence positions of the surface measurement data from the three-dimensional profile measurement device 30 are sets of points having three-dimensional coordinate values, and so the surface is extracted (surface rendering) from the MRI images, the feature locations are extracted, and the coordinate conversion equation for matching these feature locations is derived. Thereby, there is no need to undertake registration as long as the positional relationship between the head and the three-dimensional profile measurement device 30 does not change. It is possible thereby to represent spatial positional information (x, y, z coordinates) as seen from the perspective of the origin, and the positions on the MRI images which corresponds to positions of the surgical field etc. can be shown. When acquisition of the registration date is complete, the surgeon scrubs up, operating gowns are put on, the site for surgery on the patient is sterilized, and the patient is covered with a sheet (drape) to hide portions of the patient other than the exposed portion for surgical operation thereon. Operating then commences, however the intervening approximately 10 to 15 minutes is ample time for above-described registration computation processing to be carried out.

After completion of the registration as above, when surgery is to commence the surgeon indicates the start using the keyboard 14, step 118 is affirmative, and the routine proceeds to step 120. The data of the MRI images captured prior to operation is read from the HDD 20 at step 120, and the MRI images (high resolution tomographic images of the head of the patient) are displayed on the display 18 based on the read data. In this case the display is of spatial positional information (x, y, z coordinates) as seen from the navigation origin perspective. The surgeon is able to accurately judge such matters as the position of the head of the patient by reference to the above-described MRI images displayed on the display 18. It should be noted that a high resolution display may be provided for displaying MRI images, so that the MRI images may be displayed in high resolution.

When the MRI images are displayed on the display 18, the surgeon starts surgical manipulation, and this surgical manipulation includes, for example, manipulations such as insertion of the surgical instrument 36 into the head. Then, when such manipulations are carried out, it is difficult for the surgeon to judge with good precision the position at which the surgical instrument 36 is located, and the position and range to where the surgical instrument 36 should be inserted, even with reference to the MRI images displayed on the display 18. Therefore, the current processing is carried out to measure the position of the surgical instrument 36, either in real time or each time after a certain time interval has elapsed, and to combine an image of the surgical instrument 36 onto the MRI images and display the combined image on the display 18.

First measurement of the surgical instrument 36 by the three-dimensional profile measurement device 30 is instructed at step 122. As a result of this instruction the three-dimensional profile measurement device 30 emits the send-laser beam toward the surgical instrument 36. Measurement of the surgical instrument 36 (the three-dimensional coordinates of each location thereon) is undertaken by detecting (computing) the three-dimensional coordinates of the irradiation position of the laser beam, based on the position at which the return-laser beam is received on the line sensor 70 after reflection at the spheres 36A of the surgical instrument 36, while repeatedly changing the facing direction of the mirror galvanometer 66 (and the mirror 67) and moving the moveable base 56. It should be noted that when the shape of the surgical instrument 36 is measured in advance and the location of features on the surgical instrument 36 are used in place of the spheres, the location of features corresponding to the spheres may be detected by carrying out additional image processing based on the shape of the surgical instrument obtained by scanning the surgical instrument 36 with the three-dimensional profile measurement device 30. The three-dimensional coordinates of these determined locations are used for the three-dimensional positions of the spheres 36A.

At step 124 the three-dimensional coordinates of the surgical instrument 36 are derived based on the positional data of the surgical instrument 36 obtained in step 122 from the three-dimensional profile measurement device 30. The surgical instrument 36 has a known shape, and so if the position (three-dimensional coordinates) of the spheres 36A can be measured, the position of each portion of the surgical instrument 36 can be derived. Therefore each of the positions, including the position of the distal end portion 36B of the surgical instrument 36, are derived from the position (three-dimensional coordinates) of the spheres 36A. The three-dimensional coordinate of each position are coordinates in the housing-based coordinate system, and therefore the coordinate conversion equation for converting the coordinate values that have just been derived in the housing-based coordinate system to coordinate values in the MRI coordinate system is read out from the HDD 20, and the three-dimensional coordinate of each point on the surgical instrument 36 (coordinate values in the housing-based coordinate system) are respectively converted into three-dimensional coordinates in the MRI coordinate system using this coordinate conversion equation. The coordinate conversion equation for making the navigation origin the coordinate value origin is also read out from the HDD 20, and the three-dimensional coordinate values in the MRI coordinate system are respectively converted using the read-out coordinate conversion equation and the coordinate values after conversion are stored as positional data on the HDD 20. The positional alignment is thereby completed of the positional data of the surgical instrument 36, including the instrument positional data (the positional data for the unexposed portions thereof, such as the distal end portion 36B), to the three-dimensional model of the surface profile (and to the MRI images).

At step 126, a surgical instrument image is combined to show the surgical instrument 36 on the MRI images (or on the three-dimensional model of the surface profile). Namely the three-dimensional coordinate values of the surgical instrument 36 are derived in step 124. Each position of the surgical instrument image is corresponded to each position of these three-dimensional coordinate values, combining the surgical instrument image onto the MRI images. However, the surgical instrument 36 has a visibly unexposed portion (portions of the surgical instrument 36, such as the distal end portion 36B, disposed within the head of the patient, for example unexposed portions within the face surface etc. that cannot be position detected using the three-dimensional profile measurement device 30). By combining the surgical instrument image on the MRI images as described above a surgical instrument image of the unexposed portion can be displayed on the MRI images.

However, there are occasions during surgery when, depending on the progress of surgery, investigation is undertaken into how far the distal end portion of the surgical instrument should be moved (advanced). Furthermore, there are occasions when the surgical instrument 36 is positioned within the head of the patient (for example within the face surface). In the present exemplary embodiment, since the shape of the surgical instrument 36 is known in advance, the position of the unexposed portion, whose three-dimensional coordinates are not detectable with the three-dimensional profile measurement device 30, is readily determined. It is also possible to carry out virtual movement of the surgical instrument 36 by setting the movement distance.

With respect to this, at step 128, an image is generated for movement simulation processing of the surgical instrument 36. First, the destination position (expected position) is derived for a predetermined movement range, with the position of the distal end portion 36B of the surgical instrument 36 that is derived from the position (three-dimensional coordinates) of the spheres 36A as the reference position (for example, straight forward along the axial direction of the surgical instrument 36 by 5 cm; this movement amount and direction may be input by the surgeon). This destination position may be just the position of a value set in advance for the movement range, or may be the position of one or more intermediate positions with the destination position of the movement range set in advance as the end position. The three-dimensional coordinates of the single position or of each position are coordinates in the housing-based coordinate system, and the previously derived coordinate conversion equation for converting from the housing-based coordinate system to the MRI coordinate system are read out form the HDD 20, and the three-dimensional coordinates (coordinate values in the housing-based coordinate system) of the single destination position of the surgical instrument 36, or of each point, are converted to three-dimensional coordinate values in the MRI coordinate system, further converted into coordinate values with the navigation origin as the coordinate axes origin, and the positional data after conversion stored on the HDD 20. Thereby positional alignment is carried out of positional information (in particular positional data of the unexposed portion of the distal end portion 36B) for a single or plural position(s), predicted as the destination for movement amount(s) in the determined movement direction for the movement range set in advance, onto the three-dimensional biological model (and MRI images). An image can then be displayed corresponding to virtual movement of the surgical instrument 36, by generation of an image in which the single position or each of the positions is superimposed on an image of the distal end portion 36B of the surgical instrument 36.

Information is thereby effectively presented to the surgeon etc. in this manner, by showing which location would be reached when the surgical instrument is moved by a certain amount from the position of the surgical instrument. It should be noted that when plural positions are being determined for the destination position, these may be intermittent positions each at a specific interval apart, or these may be continuous positions. Also, when combining high resolution tomographic images for the surgical instrument image in the expected position image showing the surgical instrument image with the distal end portion of the surgical instrument in the single or plural destination positions, the surgical instrument image may be superimposed in plural positions in the combined image, or separate combined images may be generated for each position and these plural images output in sequence. By so doing, the position where the distal end portion of the surgical instrument will reach in the surgical field when the surgical instrument has been moved from the current position can be readily presented to the surgeon etc. It should be noted that when the above-described simulation of the movement of the surgical instrument 36 is not required the processing of step 128 is not required.

Next, in step 130, the MRI images displayed on the display 18 are refreshed by displaying on the display 18 MRI images combined with surgical instrument images from steps 126 and 128 that include the position of the distal end portion 36B of the surgical instrument 36 and the expected destination position after movement of the distal end portion 36B.

By so doing, the surgeon is able to accurately determine the state of each portion of the subject (the external and internal portions of the head of the patient) with various types of surgical manipulation during surgery, by reference to the above refreshed MRI images displayed on the display 18. Since such refreshing of the display of the MRI images is carried out repeatedly up till completion of the operation (up till when the determination is affirmative at step 132), the surgeon is able to perform surgery while checking positional relationships, such as between the position of the surgical instrument and the destination position of the surgical instrument after moving. The MRI images displayed on the display 18 may be functional mapping MRI images, with a previously investigated map of partitioning of each function superimposed thereon. When functional mapping MRI images are displayed, the surgeon is able to progress surgery while knowing the positional relationship of the site being operated on to each functional area.

The coronal section, sagittal section, and horizontal section MRI images are reconstituted in this manner with the surgical field displayed as a flashing point. In addition, as a simulation of the insertion of a bar shaped surgical instrument, for example, the destination may be calculated when an insertion of 5 cm is made in the straight forward direction, and this simulation displayed straight away on the images.

Navigation is executed in this manner during surgery. Namely, the position of the surgical instrument 36 is scanned/measured by the three-dimensional profile measurement device 30. The position of these three-dimensional coordinate values can be displayed as spatial information as viewed from the above-described origin, and displayed on the MRI images. The position of the distal end of a bar shaped surgical instrument can be calculated and displayed on the MRI images by attaching plural spheres to an end of the surgical instrument and by sensing the position of these spheres. In particular data acquisition for registration (positional alignment) is made unnecessary when this is being carried out. The reason for this is because, firstly, the surgical field is mostly covered by a surgical sheet, and cannot be seen, and secondly, because although the patient is not pinned the patient is fixed so as not to be able to move, therefore the position does not change between the scanner and the patient unless the position of the body of the patient is deliberately changed, and so the initial registration is sufficient.

However, the above registration process is preferably re-executed when the position of the patient has unexpectedly moved, or when it is desired to change the position of the patient intentionally to perform surgery thereon. In particular, since in ENT the features of the surface profile are included in the surgical field, and so necessary data for registration can be acquired during surgery (since they are not covered by a sheet). When the surface is covered by a drape, the sheet (drape) may be removed from the patient, and registration may be re-executed as described above along with any change in the housing-based coordinate system. When surgery is of the head or the like, 3 or more small marks may be made in a confined region (a region exposed through a hole in the sheet), so that registration may be repeatedly executed using these small marks. These marks are different from MRI image capture marks, and are applied to the confined region of the surgical field when initial registration is carried out, the three-dimensional surface profile for registration is measured including these marks, and registration in subsequently carried out with these marks as the reference. For surgery to the head, such as stereotactic neurosurgery, since small holes of about 1.6 mm diameter are opened in the bone rather than opening a large opening in the head, these marks are easily applied in the vicinity of such holes. This feature is specific to the surgery support device 10 of the present exemplary embodiment in which measurement of the position of the surgical instrument can be made at the same time by the three-dimensional profile measurement device 30 for acquiring the surface profile; initial registration is carried out, then from the second time onwards a simple registration can be carried out, maintaining a high navigational accuracy.

In the surgery support device 10 according to the present exemplary embodiment, as explained above, the surface profile data obtained, by optically measuring the surface of the subject (the head of the patient in the present exemplary embodiment) using the three-dimensional profile measurement device 30, is readily corresponded to the previously captured MRI images. Also, the correspondence between the three-dimensional coordinate values in the housing-based coordinate system and the three-dimensional coordinate values in the MRI coordinate system prior to surgery is easily derived, since feature locations of the face, including the ears, nose, mouth, eyes etc., can be corresponded using pattern matching between the surface profile data and the three-dimensional biological model (three-dimensional model of the surface profile). Consequently it is not necessary prior to surgery to make marks using a material that can be seen in MRI images, and it is also not necessary to robustly fix the subject, such as the head of the patient, using a frame or the like. The configuration of the device can also be simplified by using a common three-dimensional profile measurement device for measuring the position of the surgical instrument and the profile of the subject, such as the head of a patient.

It should be noted that the surgery support device 10 according to the present exemplary embodiment enables safe surgery to be performed in previously mentioned stereotactic neurosurgery, such as deep-brain stimulation and deep-brain oblation, in brain tumor exploratory surgery, in hemorrhage aspiration and the like, and also in ENT and tracheal surgery, such as radical surgery for paranasal sinus inflammation. Surgery is performed while confirming the correct dissection and optical positional relationship of the periphery and the portion being surgically manipulated whenever required, such as when surgery is started, during excision, and after excision. It is also possible to confirm the presence of residual tumor (tumor that has been left behind) to ensure complete excision. This is accomplished without the pain of applying fixings for a frame to the patient, and also without complicated marking procedures during CT/MRI image capture prior to surgery.

In the surgery support device 10 according to the present exemplary embodiment, the measurement of the surface profile using the three-dimensional profile measurement device 30 and the measurement of the position of the surgical instrument 36 are completed in about 10 seconds, therefore lost time during surgery can be greatly reduced in comparison to when MRI images are captured during surgery.

The surgery support device 10 according to the present exemplary embodiment can be executed merely by adding the three-dimensional profile measurement device 30 to the computer 12 installed with the surgery navigation programs, such as the three-dimensional model generation program and the MRI image display program, enabling realization at significantly lower cost in comparison to periodically capturing MRI images during surgery.

It should be noted that that in the present exemplary embodiment, images captured by video camera may be used corresponded with the surface measurement data and corresponded with the three-dimensional model of the surface profile. Consequently even if there are features which are not clearly discernable in the surface measurement data, such as changes in the color of the face surface, these features can be corresponded with the surface measurement data and with the three-dimensional model of the surface profile, enabling an increase in the precision of correspondence of the surface measurement data and the three-dimensional model of the surface profile.

Explanation has been given above of an example of MRI images as the high resolution tomographic images according to the present invention, however, tomographic images captured for example by X-ray CT imaging and the like, and by other known imaging methods may also be used, as long as these images are tomographic images that represent the surgical field with high resolution. Also, in addition to the high resolution tomographic images according to the present invention, when performing surgery with reference also to other tomographic images captured by another image capture method (for example Positron Emission Tomography (PET), Single Photon Emission Computed Tomography (SPECT), or the like), by corresponding in advance the other tomographic images with the high resolution tomographic images of the present invention, after correcting the high resolution tomographic images according to the present invention based on the surface profile data and the unexposed portion data as described above, the other tomographic images may also be corrected based on the post correction high resolution tomographic images, and then displayed.

In the above exemplary embodiment, as an example of a shape measurement means of the present invention explanation was given of a using three-dimensional profile measurement device for carrying out shape measurement using an optical scanning method while scanning a laser beam to obtain the three-dimensional coordinates. However, the present invention is not limited thereto. Other shape measurement devices capable of obtaining three-dimensional coordinates may be used, such as for example, a shape measurement device using a light-section method for measuring the three-dimensional position by changes in position of a line of light beam the subject when projecting the line of light onto the subject from a specific direction, or a shape measurement device using a pattern projection method for measuring the three-dimensional position by projecting a lattice of lines of light onto the subject.

Explanation has been given above of a case in which spheres have been provided to the surgical instrument, however, the present invention is not limited thereto. For example precise measurement of the surgical instrument 36 may be taken in advance, and a number of characteristic positions thereon determined in advance may be used, this number corresponding to the number of spheres that would have been used or more than this number. An effect of such an approach is to suppress any awkwardness felt by the surgeon from transitioning from using current surgical instruments to using new surgical instruments provided with the spheres. If this approach is used then characteristic positions corresponding to the spheres may be detected by image processing based on the shape of the surgical instrument obtained by scanning the surgical instrument 36 with the three-dimensional profile measurement device 30, and the three-dimensional coordinates of these detected positions processed instead of the three-dimensional coordinates of the spheres.

EXPLANATION OF THE REFERENCE NUMERALS 10 surgery support device
12 computer
18 display
22 drive
24 MRI image capture device
26 surgical microscope
30 three-dimensional profile measurement device
36 surgical instrument
81 reference point

The invention claimed is:

1. A surgery support device comprising:
a profile measurement means for optically measuring a surface of a subject and obtaining surface profile information representing the three-dimensional coordinate position of each location across an entirety of the subject surface;
input means for inputting a plurality of high resolution tomographic images of the subject captured prior to surgery;
correspondence processing means for acquiring the surface profile information obtained by the profile measurement means prior to surgery and corresponding each location on the subject surface with a surface position in the high resolution tomographic images, based on the acquired surface profile information and based on the plurality of high resolution tomographic images input by the input means;
acquisition means, provided with correction means, for acquiring surface profile information during surgery with the profile measurement means and correcting the correspondence relationship between each location of the subject surface and the surface position in the high resolution tomographic images with the obtained surface profile information, and acquiring as surface profile information three-dimensional coordinate positions of the surface of the exposed portion of a surgical instrument having a specific profile used for surgery and three-dimensional coordinate positions of each location on the surface of the subject by measuring the surface of the subject and the surface of the exposed portion of the surgical instrument using the profile measurement means during surgery, deriving the position of the exposed portion of the surgical instrument based on the acquired surface profile information and acquiring instrument position information representing the three-dimensional coordinate position of an unexposed portion including the distal end portion of the surgical instrument, based on the derived position of the exposed portion;
combining means for combining, based on the instrument position information acquired by the acquisition means, a surgical instrument image with the high resolution tomographic images such that the surgical instrument image showing the unexposed portion of the surgical instrument is aligned with each position of the unexposed portion including the distal end portion of the surgical instrument; and a display controller displaying the combined high resolution tomographic images combined by the combining means on a display.

2. The surgery support device of claim 1, wherein:

the profile measurement means comprises a scanning device that scans a light on the surface of the subject, and detection means for detecting the three-dimensional coordinate position of the location of irradiation of the light on the subject surface by receiving a reflection of the light from the subject surface; and wherein the three-dimensional coordinate position detection by the detection means is carried out repeatedly while scanning the light over each location on the subject surface.

3. The surgery support device of claim 2, wherein the light is a laser beam.

4. The surgery support device of claim 1, wherein the acquisition means estimates the three-dimensional coordinate position of the unexposed portion including the distal end portion of the surgical instrument based on the data determined in advance corresponding to a plurality of locations on the exposed portion with the specific profile.

5. The surgery support device of claim 1, wherein the high resolution tomographic images are MRI images captured by a Nuclear Magnetic Resonance-Computer Tomography method.

6. The surgery support device of claim 1, wherein the combining means for combining a surgical instrument image with the high resolution tomographic images:

derives a predicted position for when the distal end portion of the surgical instrument is moved within a predetermined movement range, based on the instrument position information acquired by the acquisition means; and further combines the high resolution tomographic images with the surgical instrument image as a predicted position image such that the surgical instrument image showing the unexposed portion of the surgical instrument is positioned at the predicted position or at one or more intervening positions up to the predicted position.

7. The surgery support device of claim 1, wherein the combining means:

derives a predicted position for when the distal end portion of the surgical instrument is moved within a predetermined movement range, based on the instrument position information acquired by the acquisition means; and further combines the high resolution tomographic images with the surgical instrument image as a predicted position image such that the surgical instrument image showing the distal end portion of the surgical instrument is positioned at a plurality of positions from the position of the distal end portion of the surgical instrument prior to movement up to the predicted position thereof, or up to an intervening position towards the predicted position.

8. A surgery support method supporting surgery by displaying, on a surgery support system provided with a display for displaying high resolution tomographic images, a surgical instrument on the high resolution tomographic images at the same time that the high resolution tomographic images are being displayed on the display during surgery, the surgery support method comprising:

optically measuring the surface of a subject;

obtaining surface profile information representing the three-dimensional coordinate position of each location across an entirety of the subject surface;

inputting a plurality of high resolution tomographic images of the subject captured prior to surgery;

acquiring the surface profile information obtained by the profile measurement means prior to surgery;

matching each location on the subject surface with a surface position in the high resolution tomographic images, based on the acquired surface profile information and based on the plurality of input high resolution tomographic images;

acquiring surface profile information during surgery;

correcting the correspondence relationship between each location of the subject surface and the surface position in the high resolution tomographic images, based on the acquired surface profile information;

acquiring three-dimensional coordinate positions of the surface of the exposed portion of a surgical instrument having a specific profile used for surgery and three-dimensional coordinate positions of each location on the surface of the subject as surface profile information by measuring the surface of the subject and the surface of the exposed portion of the surgical instrument during surgery, deriving the position of the exposed portion of the surgical instrument based on the acquired surface profile information;

acquiring instrument position information representing the three-dimensional coordinate position of an unexposed portion including the distal end portion of the surgical instrument, based on the derived position of the exposed portion;

combining a surgical instrument image with the high resolution tomographic images such that the surgical instrument image showing the unexposed portion of the surgical instrument is aligned with each position of the unexposed portion including the distal end portion of the surgical instrument; and displaying the combined high resolution tomographic images on a display.

9. A non-transitory computer readable recording medium storing surgery support program executed in a surgery support system provided with a computer connected to a display for displaying high resolution tomographic images, the surgery support program displaying a surgical instrument on the high resolution tomographic images at the same time that the high resolution tomographic images are being displayed on the display during surgery, the surgery support program causing the computer to execute processing comprising:

optically measuring the surface of a subject;

obtaining surface profile information representing the three-dimensional coordinate position of each location across an entirety of the subject surface;

inputting a plurality of high resolution tomographic images of the subject captured prior to surgery are input;

acquiring the surface profile information obtained by the profile measurement means prior to surgery is acquired;

matching each location on the subject surface with a surface position in the high resolution tomographic images, based on the acquired surface profile information and based on the plurality of input high resolution tomographic images;

acquiring surface profile information during surgery;

correcting the correspondence relationship between each location of the subject surface and the surface position in the high resolution tomographic images with the obtained surface profile information;

acquiring three-dimensional coordinate positions of the surface of the exposed portion of a surgical instrument having a specific profile used for surgery and three-dimensional coordinate positions of each location on the surface of the subject as surface profile information by switching during surgery from measuring the surface of the subject, deriving the position of the exposed portion of the surgical instrument based on the acquired surface profile information;

acquiring instrument position information representing the three-dimensional coordinate position of an unexposed portion including the distal end portion of the surgical instrument, based on the derived position of the exposed portion;

combining a surgical instrument image with the high resolution tomographic images such that the surgical instrument image showing the unexposed portion of the surgical instrument is aligned with each position of the unexposed portion including the distal end portion of the surgical instrument;

and displaying the combined high resolution tomographic images combined by the combining means on a display.

* * * * *

UNITED STATES PATENT AND TRADEMARK OFFICE
CERTIFICATE OF CORRECTION

PATENT NO. : 8,463,360 B2  Page 1 of 1
APPLICATION NO. : 12/278954
DATED : June 11, 2013
INVENTOR(S) : Yamamoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1339 days.

Signed and Sealed this
Eighth Day of September, 2015

Michelle K. Lee
*Director of the United States Patent and Trademark Office*